US010463236B2

(12) United States Patent
Simchony et al.

(10) Patent No.: US 10,463,236 B2
(45) Date of Patent: Nov. 5, 2019

(54) SEALING DEVICE FOR COLONOSCOPY PROCEDURE (71) Applicant: G.I. VIEW LTD., Ramat Gan (IL)

(72) Inventors: Tal Simchony, Hod Ha Sharon (IL); Avraham Sinay, Petach-Tikva (IL); Ilia Krivoruk, Haifa (IL)

(73) Assignee: G.I. VIEW LTD., Ramat Gan (IL)

(*) Notice: Subject to any disclaimer, the term of this patent is extended or adjusted under 35 U.S.C. 154(b) by 309 days.

(21) Appl. No.: 14/761,900

(22) PCT Filed: Jan. 21, 2014

(86) PCT No.: PCT/IL2014/050072
§ 371 (c)(1),
(2) Date: Jul. 17, 2015

(87) PCT Pub. No.: WO2014/111946
PCT Pub. Date: Jul. 24, 2014

(65) Prior Publication Data
US 2015/0351617 A1    Dec. 10, 2015

Related U.S. Application Data (60) Provisional application No. 61/754,722, filed on Jan. 21, 2013.

(51) Int. Cl.
*A61B 1/00* (2006.01)
*A61B 1/018* (2006.01)
(Continued)

(52) U.S. Cl.
CPC ...... *A61B 1/00154* (2013.01); *A61B 1/00066* (2013.01); *A61B 1/00078* (2013.01);
(Continued)

(58) Field of Classification Search
CPC ...... A61M 29/10; A61M 1/285; A61M 27/00; A61M 3/10; A61M 25/10; A61M 25/101;
(Continued)

(56) References Cited

U.S. PATENT DOCUMENTS 3,896,816 A    7/1975   Mattler
4,776,845 A    10/1988  Davis
(Continued)

FOREIGN PATENT DOCUMENTS

CN         1568203       1/2005
CN        201675970     12/2010
(Continued)

OTHER PUBLICATIONS

Martin's Arm, Artisan Medical ( www.artisanmed.com/products/martins-arm-xl-retractor) copyright 2011.*
(Continued)

*Primary Examiner* — Thomas M McEvoy
(74) *Attorney, Agent, or Firm* — Dorsey & Whitney LLP (57) ABSTRACT The present invention discloses a sealing device comprising a sealing tube having proximal and distal ends, the proximal end being adapted to be inserted through an anus of a patient; and a rectal surface mounted at the distal end of the sealing tube and positioned substantially perpendicularly to a cross section of the sealing tube. The rectal surface is configured and operable to create a pressure on the anus externally and activate anal muscles, wherein the rectal surface is placed in contact with the anus when in use.

12 Claims, 8 Drawing Sheets

(51) Int. Cl.
*A61B 1/012* (2006.01)
*A61B 10/04* (2006.01)
*A61B 1/015* (2006.01)
*A61B 1/31* (2006.01)
*A61B 17/00* (2006.01)

(52) U.S. Cl.
CPC ...... *A61B 1/00082* (2013.01); *A61B 1/00114* (2013.01); *A61B 1/00142* (2013.01); *A61B 1/00149* (2013.01); *A61B 1/015* (2013.01); *A61B 1/018* (2013.01); *A61B 1/0125* (2013.01); *A61B 1/31* (2013.01); *A61B 10/04* (2013.01); *A61B 2017/0034* (2013.01)

(58) Field of Classification Search
CPC .......... A61M 2025/0233; A61M 25/02; A61M 25/04; A61B 17/12136; A61B 17/12131; A61B 17/12022; A61B 1/31; A61B 2017/22069; A61J 15/0042
See application file for complete search history.

(56) References Cited

U.S. PATENT DOCUMENTS

| | | | |
|---|---|---|---|
| 5,941,815 A | 8/1999 | Chang | |
| 6,039,714 A * | 3/2000 | Cracauer | A61J 15/0034 604/103.03 |
| 8,500,771 B2 * | 8/2013 | Isham | A61B 5/411 606/197 |
| 8,506,537 B2 | 8/2013 | Tortstensen et al. | |
| 2007/0213661 A1 | 9/2007 | Gobel | |
| 2009/0062837 A1 * | 3/2009 | Gasche | A61B 1/00089 606/197 |
| 2009/0112186 A1 * | 4/2009 | Adams | A61J 15/0015 604/524 |
| 2009/0171280 A1 * | 7/2009 | Samuel | A61J 15/0015 604/99.04 |
| 2011/0306823 A1 | 12/2011 | Gobel et al. | |
| 2012/0031400 A1 * | 2/2012 | Shimm | A61G 13/1215 128/200.26 |
| 2012/0296272 A1 | 11/2012 | Bidault et al. | |
| 2014/0107692 A1 * | 4/2014 | Matsuo | A61M 13/003 606/192 |

FOREIGN PATENT DOCUMENTS

| | | |
|---|---|---|
| EP | 1782726 | 5/2007 |
| FR | 2480127 | 10/1981 |
| FR | 2896167 | 7/2007 |
| WO | WO2011/126812 | * 10/2011 |

OTHER PUBLICATIONS

International Search Report for International Application No. PCT/IL2014/050072 dated Aug. 5, 2014.

* cited by examiner

SEALING DEVICE FOR COLONOSCOPY PROCEDURE

FIELD OF THE INVENTION

The present invention relates generally to medical devices, particularly those devices that can be inserted into a body cavity of a patient.

BACKGROUND OF THE INVENTION

Endoscopy has become an increasingly important tool in diagnosing and in treating ailments of the gastrointestinal tract, also referred to as the GI tract. Typical endoscopes are essentially formed by a somewhat flexible tube that is pushed through the GI tract, after being introduced into the body cavity either at the rectum or from the esophagus. The endoscope has a steerable tip to facilitate navigation through the GI tract, and typically has to be sufficiently stiff so that it can be pushed further along the body cavity. The tip of the endoscope that is introduced in the GI tract can be fitted with several devices, most notably an illumination device and a vision device, such as a vision integrated circuit, so that the operator of the endoscope can observe the interior of the GI tract and maneuver the endoscope into the proper position.

A colonoscopy is the visual examination of a patient's colon from a remote location through the use of instrumentation. In examining the colon, an instrument known as a colonoscope is used. During an endoscopy, the scope is inserted in the anus, through the rectum, sigmoid colon, descending colon, transverse colon, ascending colon and then into the cecum. Advancing the scope, which is typically about 160 centimeters in length, can be difficult due to a loop in the sigmoid colon. Once the scope reaches the descending colon or transverse colon, this loop must be reduced by withdrawing the scope to a straightened position. Failure to straighten the loop in the sigmoid colon prior to continuing can cause enlargement of the loop and result in pain and injury, including adverse cardiac reactions such as hypotension and bradycardia. Once the loop is straightened, further advancement of the endoscope can usually be accomplished. In patients having long sigmoid colons, reaching the cecum may be extremely difficult, if not impossible, due to reformation of the sigmoid loop when the operator attempts further advancement of the scope. Continued pushing of the scope under these circumstances enlarges the loop, rather than advancing the tip of the scope. Scope operators often employ various maneuvers to complete the examination, including changing the patient's position and the use of abdominal compressions. Unfortunately, these maneuvers prolong the procedure and are not always successful in helping the scope reach the cecum. Even expert colonoscopists experience difficulties in 10-20 percent of cases because of the long sigmoid colon problem. The overall success rate for total colonoscopy, i.e. getting the tip of the colonoscope to the cecum, has been reported to be 55-98 percent. Moreover, during the colonoscopy, a sensing tube is inserted into the colon via either the anus or a stoma in the patient's abdominal wall and the colon is inflated with an insufflation means to aid the surgeon's examination. Inflation of the colon makes examination easier and reduces the risk of injury. In the past, surgeons have relied exclusively upon the sphincter muscles ringing the anus to provide a seal around the sensing tube. This seal is necessary to maintain the colon in an inflated condition and prevent the discharge of fecal material during examination. However, the sphincter muscles relax after the administration of sedation and in older patients, thus reducing the seal around the colonoscope sensing tube and increasing the difficulty of the examination. In an examination through a stoma, there are no sphincter muscles to provide a seal.

Davis, U.S. Pat. No. 4,776,845 describes an apparatus that is designed for insertion into the rectum or stoma of a human being. The rectal-stomal insert apparatus is provided with an instrument channel for receiving the colonoscope sensing tube and a suction channel for allowing suctioning of fecal material from the colon. The colonoscope sensing tube is inserted into the colon through the instrument channel, wherein the examination can commence.

GI View Ltd which is the assignee of the present application, has developed a system comprising inter alia a piston head coupled to a distal portion of the carrier and adapted to form a pressure seal with a wall of the lumen after the carrier has been inserted into the lumen, and be advanced distally through the body lumen in response to pressure from the fluid pressure source. The inflatable balloon forms a sealing contact with the wall of the body lumen to enable a medical device to propel by rear pressure through a body lumen. The piston head is adapted to be inflated so as to form and maintain the pressure seal with the wall of the GI tract. To enable the advancement of the piston head distally through the body lumen in response to pressure from the fluid pressure source, the GI tract should be inflated with gas (generally $CO_2$) and the anus should be sealed. This procedure is performed regularly using a sealing device inserted via the anus. The device contains an inflatable sealing balloon made of silicon or some other type of conforming material. However, most patients cannot hold such a balloon inside the rectum as pressure in the colon increases, causing them to eject the balloon from the anus.

GENERAL DESCRIPTION

The inventors of the present invention have found that the anal sphincters of a patient can be stimulated and contract by themselves by creating gentle pressure on the anus externally. The invention involves the use of a rectal sealer/surface placed on an external part of the sealing device that is gently pushed against the anus external to the body, during the procedure. The inventors have found that when the perpendicular surface is in contact with the anus, the rectum muscles contract by themselves, involuntarily.

Therefore according to one broad aspect of the present invention, there is provided a sealing device comprising: a sealing tube having proximal and distal ends, said proximal end being adapted to be inserted through an anus of a patient; and a rectal surface mounted at the distal end of the sealing tube and positioned substantially perpendicularly to a cross section of the sealing tube; the rectal surface being configured and operable to create a pressure on the anus externally and activate anal muscles, wherein the rectal surface is placed in contact with the anus when in use.

In some embodiments, the sealing tube comprises a first passageway connectable to a source of fluid pressure and being operable to convey fluid pressure into a colon when the sealing tube is inserted into the colon. The sealing tube thereby allows application of the fluid pressure upon inner walls of the colon.

In some embodiments, the device of the present invention comprises a rectal balloon mounted on the sealing tube at a certain distance from the perpendicular surface which when inflated also applies pressure on the anus internally. In this way, a pressure seal is achieved from both sides of the anus to assure that inflation gases supplied to the colon do not escape. The configuration of the sealing device of the present invention, comprising a rectal balloon at one side and a perpendicular surface at the other side, provides a strong tightening mechanism.

In some embodiments, the sealing tube may comprise a second passageway connectable to a source of fluid pressure and is operable to inflate/deflate the rectal balloon. When positioned inside the colon, the rectal balloon is inflated via the second passageway, and the fluid pressure source applies a pressure force from the inner surface of the balloon against the anus internally to generate a pressure seal.

In some embodiments, the certain distance between the rectal surface and the rectum is adjustable in order to adapt the force applied on the anus. The perpendicular surface can be moved linearly along the sealing tube closer or farther away from the anus, thus enabling control of the pressure applied on the anus from outside. Optimum sealing can be achieved when rectal balloon is fully inflated and the perpendicular surface is in a contact with the anus.

In some embodiments, the certain distance between the rectal balloon and the perpendicular surface is selected to prevent escape of fluid pressure out of the colon. The device of the present invention is configured and operable to seal between the colon and the sealing tube in a rectal area and to prevent the escape of inflation gases supplied into the colon and out of the colon.

In some embodiments, the sealing device is configured to be used with an endoscopic system. The endoscopic system comprises an elongated carrier arranged for sliding movement through the sealing tube and traverses the descending colon up to the splenic flexure. An image-capturing device, as well as at least one inflatable balloon may be mounted on the carrier. The perpendicular surface is configured as a stop preventing the insertion of the sealing tube into the colon to the length of the elongated carrier. The elongated carrier is usually manually slid/pushed through the flexible sealing tube until it reaches the traverse colon.

In some embodiments, the sealing device comprises at least one mechanical seal through which the elongated carrier or a tool passes. The elongated carrier or a tool can slide in and out of the colon while preventing fluid leakage. The mechanical seal is located within the sealing tube and comprise at least one passageway for inserting at least a tool therethrough.

In some embodiments, the elongated carrier comprises a plurality of auxiliary tubes further comprising at least one of an electrical cable, a hollow tube shaped to define a lumen for passage therethrough of a tool, and a hollow tube shaped to define a lumen for passage therethrough of a fluid.

In some embodiments, the elongated carrier comprises a third passageway for passing therethrough a tool selected from at least one of an endoscopic tool, a elongated carrier, an imaging device, an illumination device, a biopsy collecting tool, an optical device, a fluid device, and a treatment tool.

In some embodiments, the sealing tube has a diameter selected to enable the passage of at least one of the tool and of the elongated carrier therethrough.

In some embodiments, the sealing tube has a length selected to enable its insertion such until an end of a sigmoid colon curvature of a patient.

In some embodiments, the sealing tube comprises a sleeve reinforced by a spring element placed along its length to provide a predetermined stiffness selected to enable insertion of the sealing tube through the anus and navigation of at least one of the tool and the elongated carrier within the colon. The stiffness of the sealing tube is selected to be higher than the stiffness of at least one of the tool and the elongated carrier.

In some embodiments, the sealing device comprises a handle having a handle axis configured for handling the sealing device. The rectal surface and the sealing tube are mounted on the handle. The rectal surface is substantially perpendicular to the handle's axis. The sealing device may also comprise a stand configured to support the handle. The surface of the handle perpendicular to the handle axis may have any geometrical shape which applies pressure on the anus externally.

In some embodiments, at least one of the tool and the elongated carrier is humidified when in use by applying at least one of the following: at least one of the tool and the elongated carrier is coated with a hydrophilic coating; the sealing device comprises a cavity containing water-based solution through which at least one of the tool and the elongated carrier passes; the sealing tube has a curved shape to thereby enable confining of a water-based solution in the sealing tube. The cavity containing the water-based solution may be located within the handle. The cavity may comprise a porous material, such as a sponge, for controlled humidification. The cavity may pass through the first passageway conveying gas (e.g. $CO_2$) into a colon; such that the gas contains water particles to thereby enable humidification of at least one of the tool and the elongated carrier.

In some embodiments, the elongated carrier comprises a coating of a lubricious material.

In some embodiments, the sealing device is an integral part of an endoscopic system.

According to another broad aspect of the present invention, there is provided a method for stimulating an anal sphincter of a patient. The method comprises positioning within the rectum of a patient a sealing tube having a rectal surface mounted at the distal end of the sealing tube and positioned substantially perpendicularly to a cross section of the sealing tube; placing the rectal surface in contact with the external surface of the anus; and; creating pressure on the anus from externally to thereby stimulate the anal sphincter.

In some embodiments, the method comprises conveying a fluid pressure into a colon to thereby allow application of the fluid pressure upon the inner walls of the colon.

In some embodiments, the method comprises inflating a rectal balloon mounted on the sealing tube at a certain distance from the rectal surface and applying pressure on the anus internally.

In some embodiments, the method comprises humidifying a tool or a elongated carrier passing through the sealing tube by applying at least one of the following: coating at least one of the tool and the elongated carrier with a hydrophilic coating; providing a cavity containing water-based solution through which at least one of the tool and the elongated carrier passes; and confining a water-based solution in the elongated carrier.

In some embodiments, the method comprises mounting the sealing tube on a stand to thereby enable single user operation.

BRIEF DESCRIPTION OF THE FIGURES

In order to understand the invention and to see how it may be implemented in practice, preferred embodiments will now be described, by way of non-limiting example only, with reference to the accompanying drawing, in which FIG. 1A schematically illustrates a sealing device of the present invention for use in a colon of a patient.

DETAILED DESCRIPTION OF EMBODIMENTS

Figure 1A:
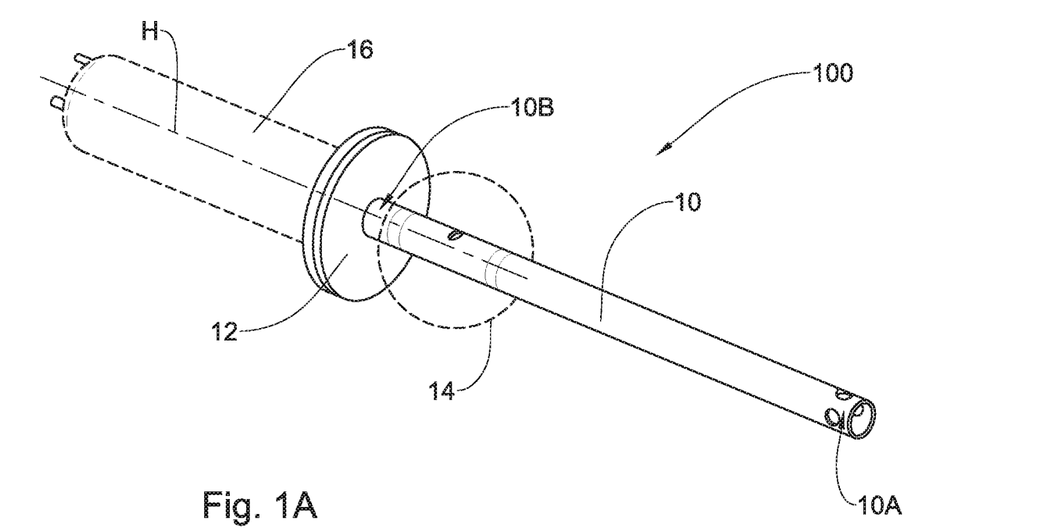

Reference is made to FIG. 1A, representing a perspective views of the sealing device of the present invention. The sealing device 100 comprises a sealing tube 10 having proximal end 10A and a distal end 10B and a rectal surface 12 mounted at the distal end 10B of the sealing tube and positioned substantially perpendicularly to a cross section of the sealing tube 10. The proximal end 10A is adapted to be inserted through an anus of a patient. The rectal surface 12 is placed in contact with the anus when in use and is configured and operable to create pressure on the anus externally and activate anal muscles. In some embodiments, the sealing device 100 comprises a handle 16 having a handle axis H configured for handling the device and a rectal balloon 14 mounted on the sealing tube 10 at a certain distance from the rectal surface 12 and configured for sealing the rectum internally after the device has been introduced inside the colon. The rectal balloon 14 applies pressure on the anus internally when inflated. The rectal surface 12 and the sealing tube 10 are mounted on the handle 16. The rectal surface 12 is substantially perpendicular to the handle's axis. The handle may be made of two parts due to manufacturing considerations or may be a single part.

In the present non-limiting example, the geometrical shape of the perpendicular surface 12 is circular. However, the perpendicular surface may also be an oval, round or any other disk shape. The handle 16 allows comfortable operation and may comprise the perpendicular surface 12 that applies pressure on the rectal opening.

Figure 1B:
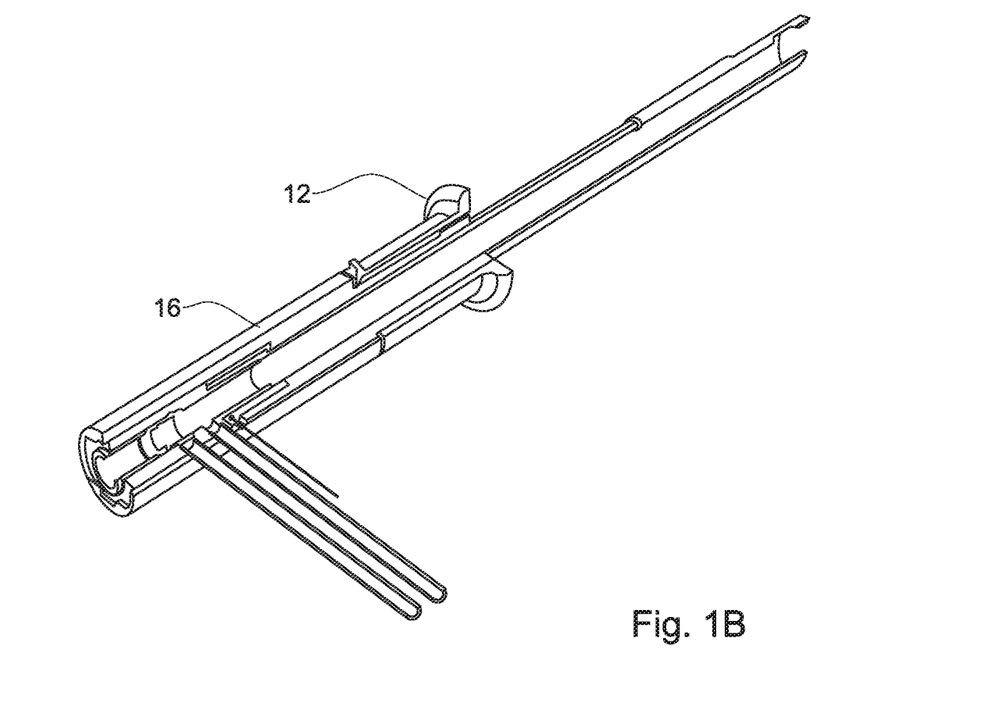
FIG. 1B schematically illustrates a portion of the sealing device with an adjustable perpendicular surface according to a specific example of the present invention.

Reference is made to FIG. 1B illustrating the ability to adjust the distance between the rectal surface 12 and the rectum in order to adapt the force applied on the anus. The distance between the perpendicular surface 12 and the rectal balloon 14 can be adjustable and is selected such that the fluid pressure (e.g. inflation gases) cannot escape out of the colon. In some embodiments, the plane of the rectal surface 12 is adjustable such that the pressure on the anus can be controlled during the operation. Although not shown, the distance between the rectal balloon and the rectal surface can also be adjusted when the device during the procedure. Perpendicular surface 12 adjustment is achieved by sliding the surface linearly over the handle 16 back and forth. The perpendicular surface 12 may be mounted on a sheath moving linearly together with the perpendicular surface 12 when adjusted. The surface 12 may be locked in an adjusted position by any method known in the art, for example by using a toothed ratchet mechanism. When the flexible sealing tube 10 is inserted within the colon, the balloon 14 is in its deflated state and is inflated after the flexible sealing tube 10 is introduced within the colon. As described above, the position of the rectal balloon 14 along the flexible sealing tube 10 is appropriately selected to ensure a pressure seal and prevent escape of the inflation gases out of the colon.

Figure 1C:
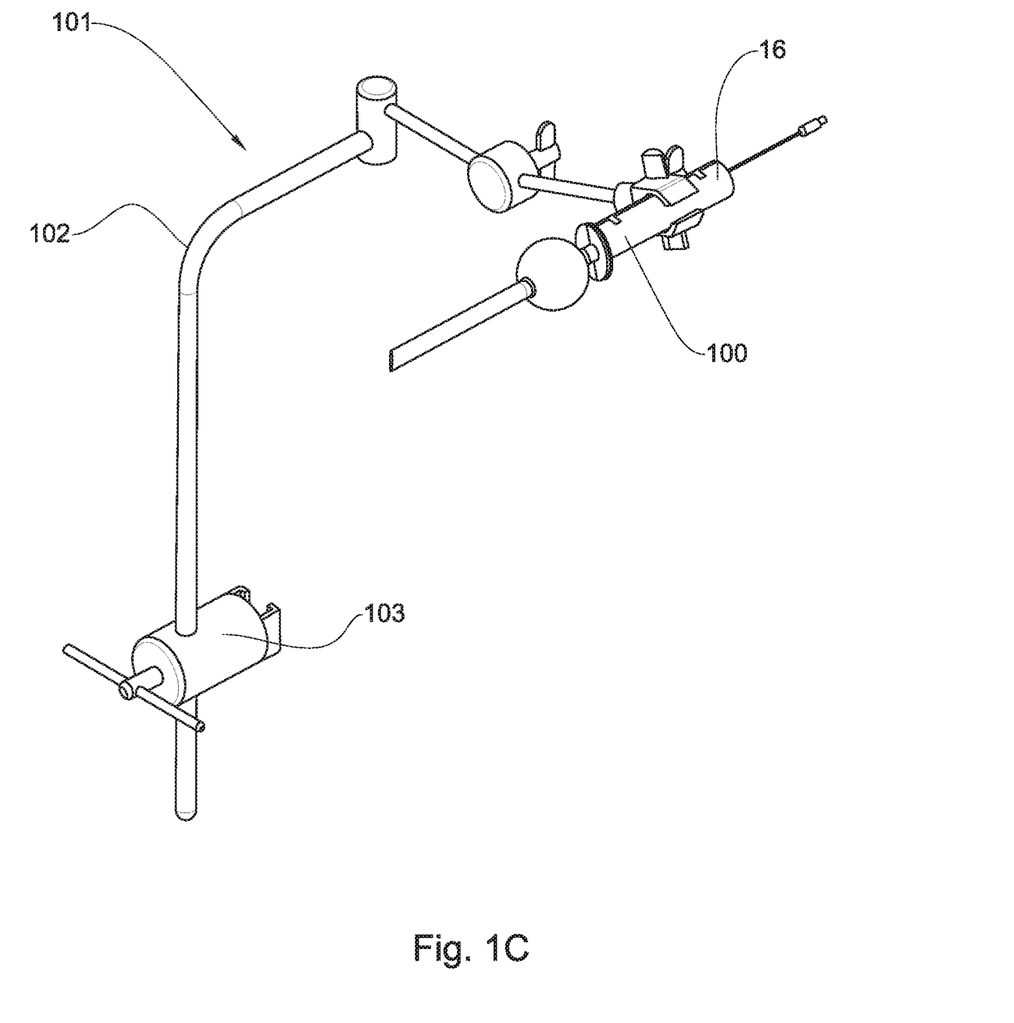
FIG. 1C schematically illustrates the sealing device mounted on a supporting stand according to a specific example of the present invention.

Reference is made to FIG. 1C illustrating the ability of the sealing device of the present invention to be suitable for single-user use. In this example, the handle 16 is supported by a stand 101 enabling the operation of the sealing device as well as the endoscopic device by a single user. In this connection, it should be understood that conventionally, the user has to handle the handle, pass the elongate carrier or a tool within the handle and activate a joystick according to the user's operation. This novel configuration renders the endoscopic device suitable for single-user use. Therefore, by using this configuration, mounting the sealing device on a stand enables single user operation. In this specific and non-limiting example, the stand 101 comprises a supporting arm 102 gripping the handle 16 of the sealing device 100 at its distal end. The supporting arm 102 includes at its proximal end a connector 103 configured to fasten the supporting arm 102 to any object such as the patient's bed. The user should therefore only activate the joystick and pass the elongate carrier or a tool within the handle.

Figure 2:
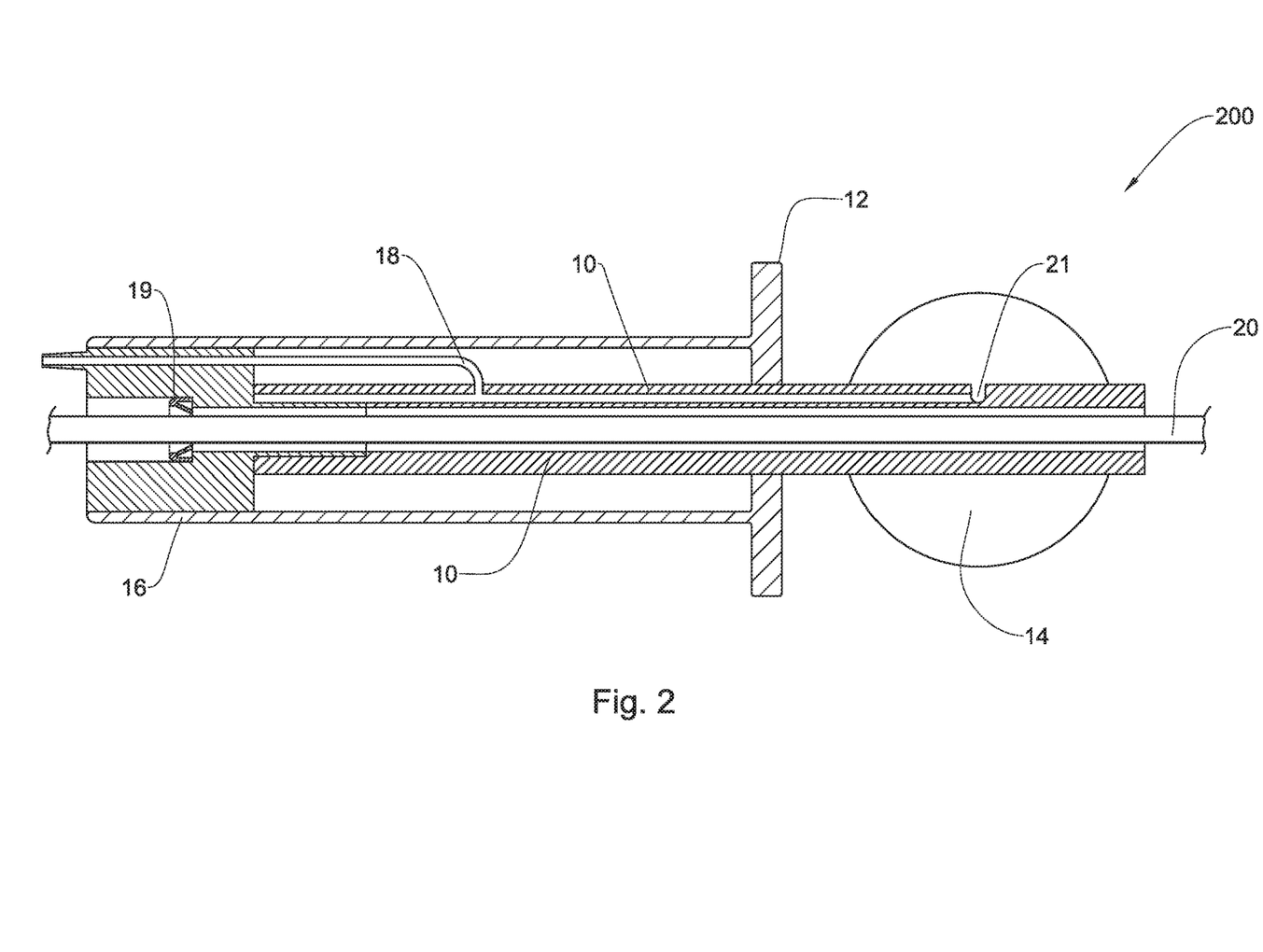
FIG. 2 illustrates a cross-sectional view of the sealing device of FIG. 1A according to some embodiments of the present invention.

Reference is made to FIG. 2, representing a detailed view of a part of the sealing device of the present invention. In some embodiments, the sealing device 200 comprises a balloon inflation channel 18 connectable to a source of fluid pressure and to a passageway passing through the sealing tube 10 configured for inflating and deflating the rectal balloon 14. The sealing tube 10 has an opening 21 located within of the rectal balloon 14 and the inflation channel supplies fluid pressure through the passageway to inflate and deflate the rectal balloon 14.

In some embodiments, the sealing device 200 may be configured to be used with an endoscopic system. The sealing tube 10 may be used to introduce any endoscopic device into a colon. The sealing device of the present invention may be configured as an integral part of an endoscopic system or may be configured as a separate device to be adapted to any endoscope device (e.g. through which an elongate carrier passes). If the sealing device is configured to be coupled with an endoscopic tool, the sealing tube 10 may be used as a guide for the elongated carrier 20. The elongated carrier 20 is arranged to enable sliding movement through the sealing tube 10. The elongated carrier 20 is usually manually slid/pushed through the flexible sealing tube until it reaches the traverse colon. The elongated carrier 20 passes through a mechanical seal 19. Seal 19 is configured to prevent fluids (e.g. $CO_2$ and water) leakage between the elongated carrier 20 and the sealing tube 10 out of the body lumen. The mechanical seal 19 is located within the sealing tube 10 and comprise at least one passageway for inserting at least a tool therethrough. The mechanical seal may have any suitable shape, such as but not limited to O-Ring, V-Ring, flat seal, membrane or other shape. The seal may be made of any conventional material like silicone, rubber or any other material used in the seal manufacturing field.

Figure 3:
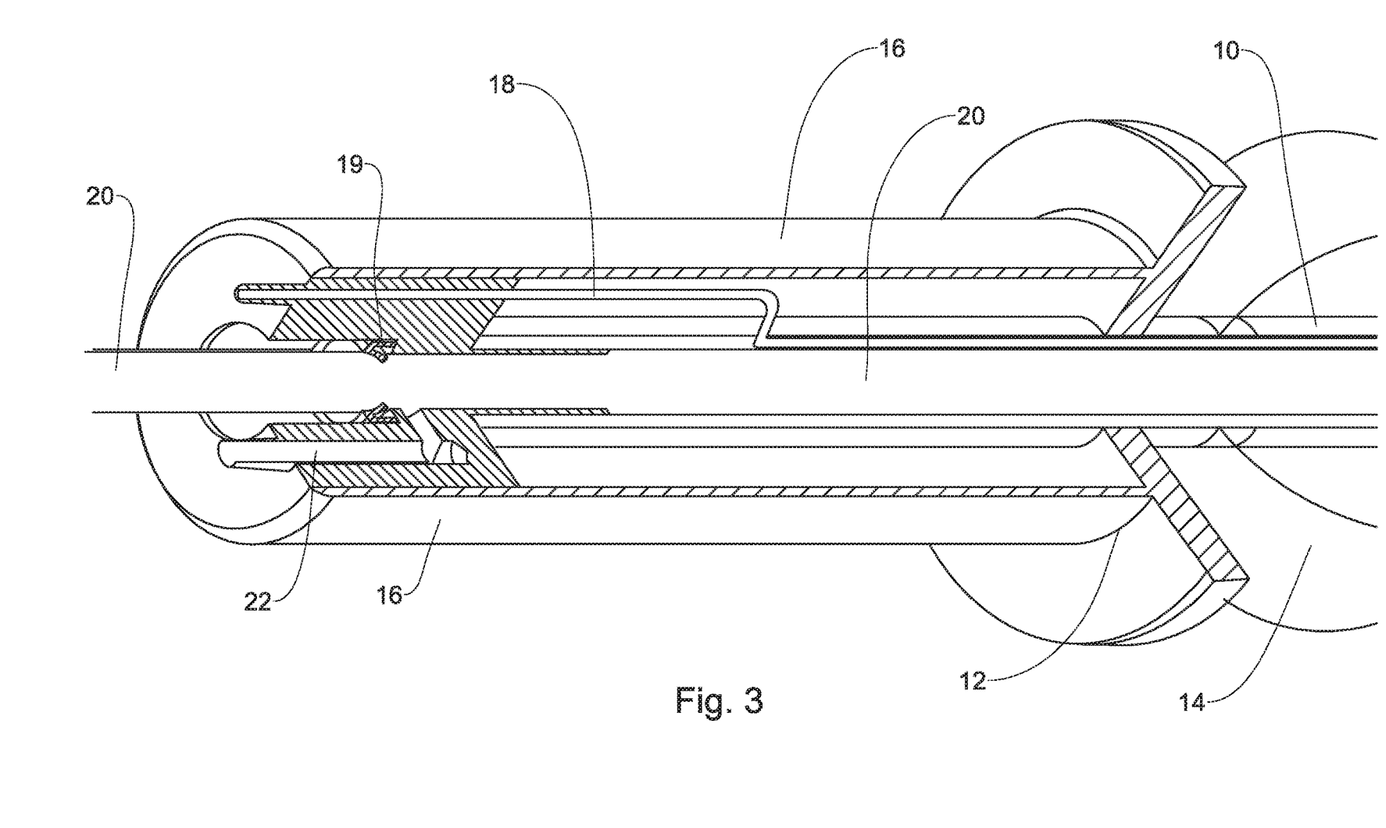
FIG. 3 illustrates a cross-sectional perspective enlarged view of the handle of the sealing device of FIG. 1A according to some embodiments of the present invention.

Reference is made to FIG. 3, representing another detailed view of a part of the sealing device of the present invention. In this example, the sealing tube 10 comprises a passageway 22 connectable to a source of fluid pressure and being operable to convey fluid pressure into a colon when the sealing tube 10 is inserted into the colon. The passageway 22 is located in the handle 16 and is configured to supply fluids (e.g. $CO_2$ and water) to the colon. The fluid is conveyed from passageway 22 to the space between the sealing tube 10 and the elongated carrier 20 until it exits to the colon. The fluid applies pressure on the colon inner walls. The seal 19 prevents backflow of fluids out of the body. In cases where the sealing device of the present invention is to be used with a piston head as described in previous GI View patent and patent applications, fluid pressure is supplied proximally to the piston head to push the piston head distally.

It should be understood that the appropriate selection of flexibility, length and diameter of the flexible sealing tube is a novel aspect of the present invention. As described above, the flexible sealing tube is configured to enable the passage of at least one tool and an elongated carrier therein, thus an appropriate diameter has to be selected. The length of the sealing tube is selected such that the flexible sealing tube can be inserted until it reaches the end of the sigmoid colon curvature.

On the one hand, the sealing tube has to be sufficiently flexible to be easily inserted in a body lumen. Tubular organs in the body may have a convoluted cavity configuration. The gastrointestinal tract, for example, starts from the oral cavity and proceeds through the esophagus, stomach, duodenum and small intestine, which is a long tube that folds many times to fit inside the abdomen. On the other hand, considering that the elongated carrier is usually very flexible, the flexible sealing tube has to be stiffer than the elongated carrier to enable its navigation within the body lumen. The flexible sealing tube may thus be configured as a sleeve reinforced by a spring element along its length to provide a predetermined stiffness selected to enable insertion of the sealing tube through the anus and navigation of the tool or elongated carrier within the colon.

Figure 4A:
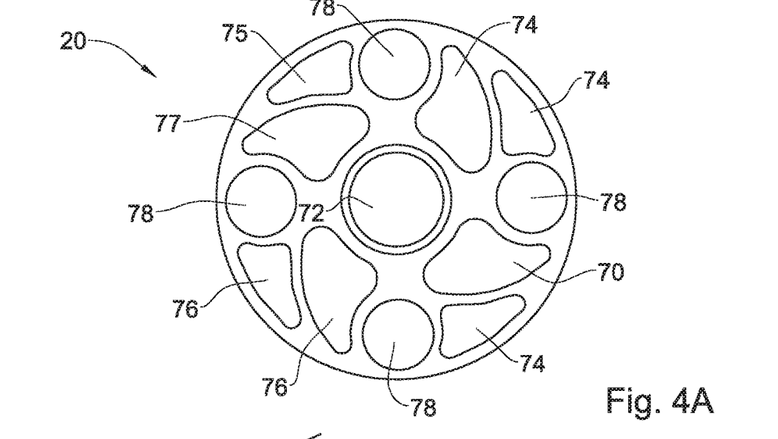
FIGS. 4A-4C schematically illustrate different views of the elongated carrier to be used with the sealing device of the present invention according to some embodiments of the present invention.
Figures 4B, 4C:
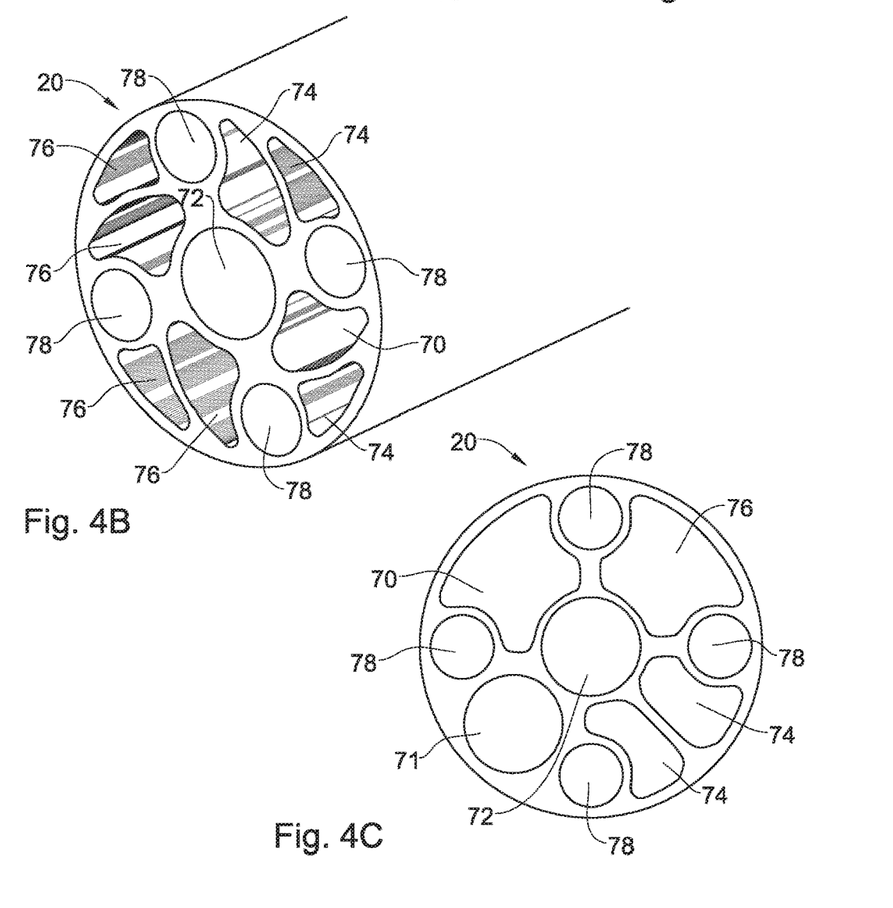

Reference is made to FIGS. 4A-4C schematically illustrates different views of the elongated carrier of the sealing device according to some embodiments of the present invention. In some embodiments, the elongated carrier 20 comprises a plurality of channels through which a plurality of auxiliary tubes may pass. The channels may be configured for supplying water 70 and inflating at least one inflatable device 74 (e.g. piston head and auxiliary piston head balloon). The elongated carrier 20 may also comprise at least one suction channel 76 that may comprise a vent tube through which fluid is ventable to the outside. The vent tube may pass through an inflatable balloon and have an opening distal to the balloon. Additionally or alternatively, the suction channel 76 may be adapted to be coupled to a suction source, whereby to actively facilitate the passage of the fluid out of the lumen. The elongated carrier 20 may also comprise an electrical channel 72 configured for at least one of transmitting an image (e.g. video) from the image capturing device on the tip of the device, illuminating the body lumen (e.g. colon), controlling various inflatable device ("balloon") pressures sensing various inflatable device ("balloon") pressures, and sensing body lumen's pressures (e.g., sensing pressure distal to apparatus). The elongated carrier 20 may also comprise at least two steering channels 78 for accommodating therein at least two steering wires respectively.

FIG. 4B illustrates a perspective view of the cross section of the elongated carrier 20 according to the specific and non-limiting example of FIG. 4A. FIG. 4C illustrates another example in which the elongated carrier 20 includes a water channel 70, an electrical channel 72, four steering channels 78 for accommodating the steering wires, a suction (venting) channel 76 configured facilitate the passage of fluid and particles out of the lumen, at least one inflation channel 74 for inflating at least one inflatable device respectively and a tool channel 71 being configured as a hollow tube shaped to define a lumen for passage therethrough of a tool. In some embodiments, the elongated carrier 20 may comprise a plurality of auxiliary tubes passing therethrough. The multi-lumen configuration alters the flexibility of the sealing tube and therefore if the elongated carrier is a multi-lumen tube, the flexibility of the reinforced flexible sealing tube should be selected with respect to the multi-lumen tube. The tool may be selected from at least one of an endoscopic tool, an imaging device, an illumination device, a biopsy collecting tool, an optical device, a fluid device, and a treatment tool.

Although not illustrated, a tool can also pass through the sealing tube. The tool can replace the elongated carrier, if the system does not include an elongated carrier. Alternatively, the tool can be accommodated adjacent to the elongated carrier if the elongated carrier is also inserted in the system together with the tool through the same passageway.

In a non-limiting example, the flexibility of the sealing tube is thus appropriately selected to be a standard endotracheal tube with an inner diameter of about 9.5 mm. As described above, the flexible sealing tube comprises a channel for inflating the rectal balloon. In a non-limiting example, the channel has a diameter of at least 1.5 mm; the reinforced flexible sealing tube may have an external diameter of 13 mm and an inner diameter in the range of about 9.5-9.8 mm.

In a non-limiting example, the rectal balloon has an outside diameter (OD) of 40-60 mm and may be made of silicon, PVC, polyurethane (PU) material, or some other type of conforming material. The certain distance between the center of the rectal balloon and the perpendicular surface may be about 15-20 mm. The selection of the appropriate material and diameter of the balloon have also two benefits; inflation with a relatively low pressure, thus avoiding any risk of injury and ability to better fit to the rectal anatomy, creating a better seal. The sealer device is configured such that friction force between the endoscope and the sealer device is less than 50 grf by appropriately selecting the seal shape and material and by humidifying the elongated carrier or a tool sliding through the sealer device during the procedure as will be described below with respect to FIGS. 6A-6B.

Figure 5A:
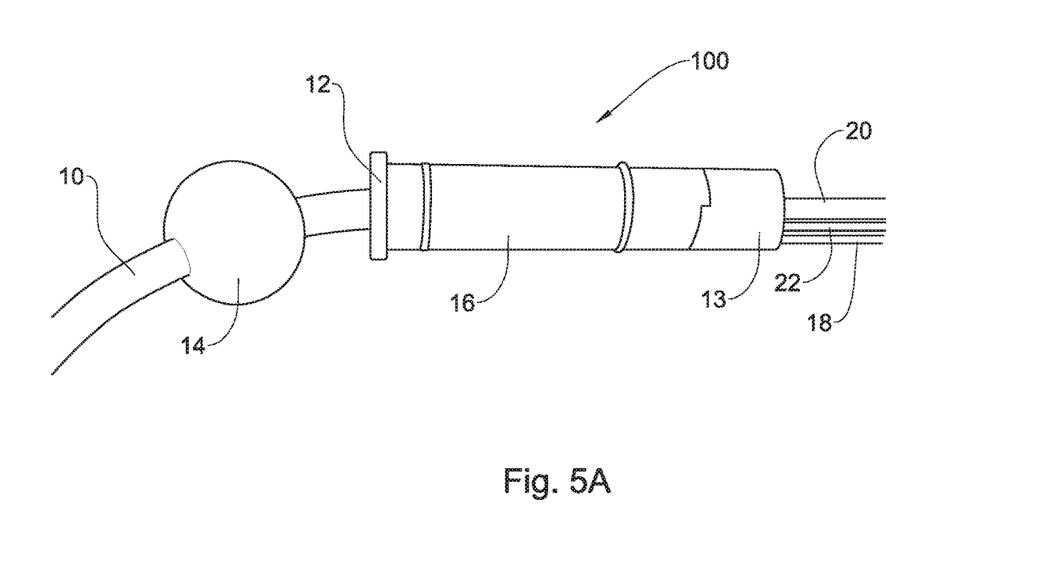
FIGS. 5A-5B are pictures illustrating the sealing device according to a specific example of the invention.
Figure 5B:
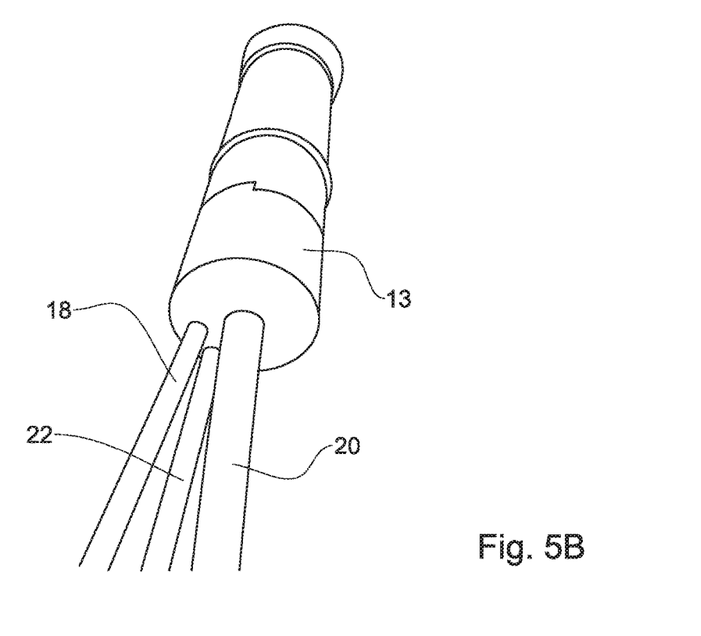

Reference is made to FIGS. 5A-5B, representing pictures of a non-limiting example of the sealing device of the present invention, through which an elongated carrier configured for imaging a body lumen or a tool, passes. FIG. 5A is a side view of the device, and FIG. 5B is a top view of the device in which the channels of the inflation of the rectal balloon 18 and of the fluid pressure supply 22 are shown.

The sealing device 100 comprises a connector 13 through which the passageways of the device and the sealing tube 10 pass. For example, the passageways include a $CO_2$ supply passageway 22 configured for supplying $CO_2$ into the colon and the rectal balloon inflation passageway 18 for supplying/sucking air for the rectal balloon inflation/deflation. In some embodiments, the connector 13 may also include seal 19 that prevents fluid leakage between the elongated carrier 20 and the connector 13. In FIG. 5B, the sealing tube 10 exiting the connector 13 is not shown. The connector 13 may be configured as an integral part of the handle or a separate part mounted on the handle.

The invention provides a novel method for stimulating an anal sphincter of a patient. The stimulating method comprises positioning within the rectum of a patient a sealing tube 10 having a rectal surface 12 mounted at the distal end of the sealing tube and positioned substantially perpendicularly to a cross section of the sealing tube; placing the rectal surface 12 in contact with the external surface of the anus; and creating pressure on the anus externally to thereby stimulate the anal sphincter.

In some embodiments, the method comprises conveying a fluid pressure (e.g. via passageway 22) into a colon to thereby allow application of the fluid pressure upon the inner walls of the colon.

In some embodiments, the method comprises a rectal balloon 14 mounted on the sealing tube 10 at a certain distance from the rectal surface 12 and applying pressure on the anus internally by inflating the balloon.

Figure 6A:
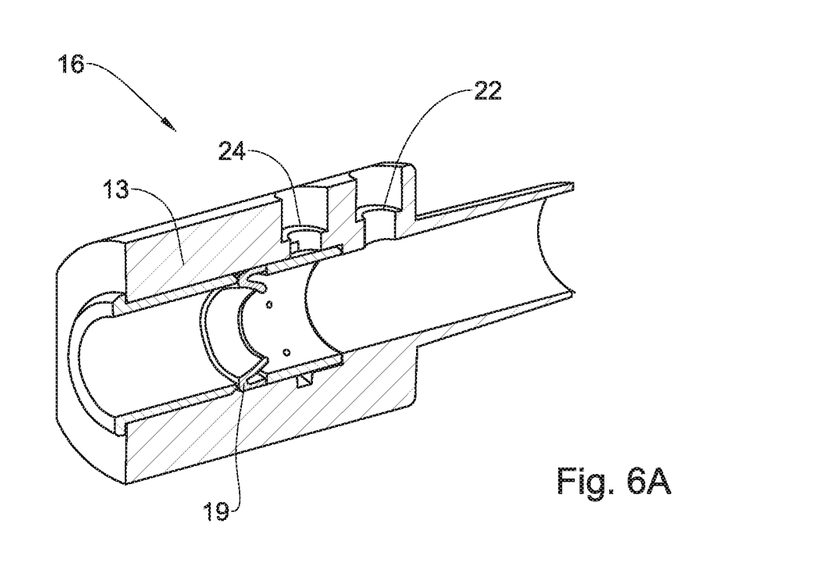
FIGS. 6A-6B illustrate a cross-sectional perspective enlarged view of possible configurations of the handle of the sealing device of FIG. 1A according to some embodiments of the present invention.
Figure 6B:
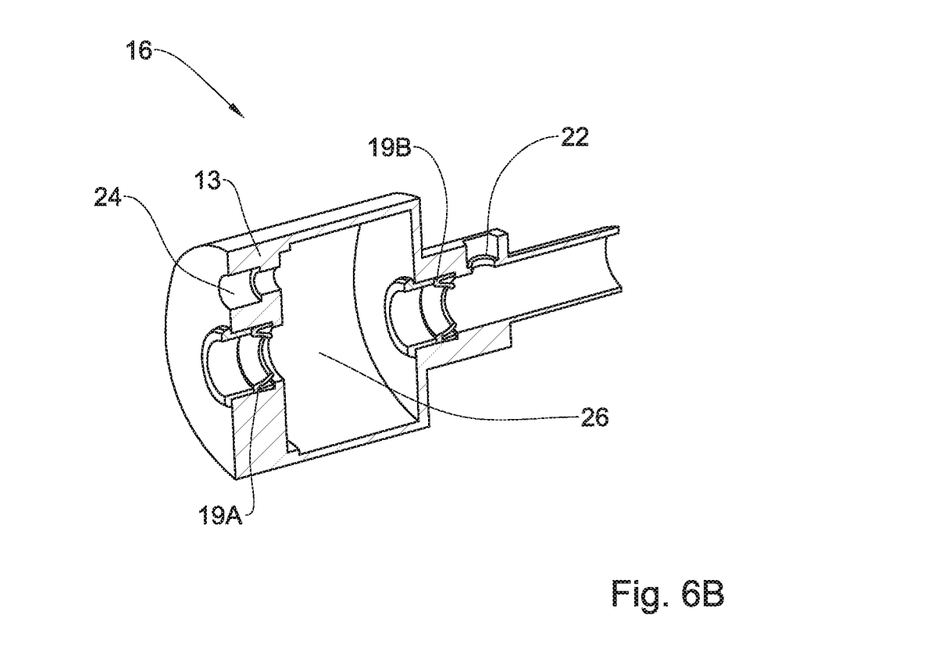

Reference is made to FIGS. 6A-6B illustrating a part of the sealing device of FIGS. 5A-5B. In some embodiments, for navigation purposes, at least one of the tool and the elongated carrier sliding through the sealer device is humidified during the procedure. The elongated carrier or the tool may be coated by using any hydrophilic coating known in the art, such as hyaluronic acid based coatings. To this end, at least one of the tool and the elongated carrier may be coated by using a hydrophilic coating. A coating of a lubricious material such as a gel, for example a gel of silicone or Teflon™ (PTFE) may be applied around the interior and/or exterior surfaces of the elongated carrier before use for ease of passage of the elongated carrier relative to the tube and/or relative to a colon. Alternatively, the coating of lubricious material may be provided as part of the elongated carrier/the tool, such as by fixing the coating to the elongated carrier/tool, or by providing the coating integral with the elongated carrier/tool.

Therefore, there is provided a novel technique for humidifying a tool or a elongated carrier passing through the sealing tube by applying at least one of the following: coating at least one of the tool and the elongated carrier with a hydrophilic coating; providing a cavity containing water-based solution through which at least one of the tool and the elongated carrier passes; confining a water-based solution in the sealing tube.

In some embodiments, the handle 16 of the sealing device comprises a channel 24 for direct water lubrication, the connector 13 through which the passageways of the device and the sealing tube 10 pass; a mechanical seal 19 configured to prevent fluid leakage between the elongated carrier and the sealing tube out of the body lumen and a passageway 22 connectable to a source of fluid pressure and being operable to convey fluid pressure into a colon when the sealing tube 10 is inserted into the colon.

FIG. 6B illustrates an embodiment in which the handle 16 of the sealing device further comprises a cavity 26 for trapping water-based solution accommodated in the connector 13. Two seals 19A and 19B prevent water leakage out of the body through connector 13 when the elongated carrier is inserted.

The wetting of the tool or of the elongated carrier can also be provided by at least one of: a water-based solution is injected via channel 24 between the sealing tube and the elongated carrier; the tip of the flexible sealing tube forms an S-shaped curve in a colon that assists in trapping the water-based solution in the flexible sealing tube as will be illustrated below in FIG. 7; a water-based solution is trapped in the cavity 26 located within the handle through which at least one of the tool and the elongated carrier passes. The cavity 26 may comprise a porous material such as a sponge for controlled water lubrication. The first passageway 22 passes through the cavity 26 conveying gas (e.g. $CO_2$) into a colon; such that the gas contains water particles to thereby enable humidification of at least one of the tool and the elongated carrier. In this way, the $CO_2$ passes through the same channel containing water, providing a "wet $CO_2$" to enable keeping the lumen wet.

In some embodiments the first passageway 22 and the channel 24 can be combined to a single passageway.

Figure 7:
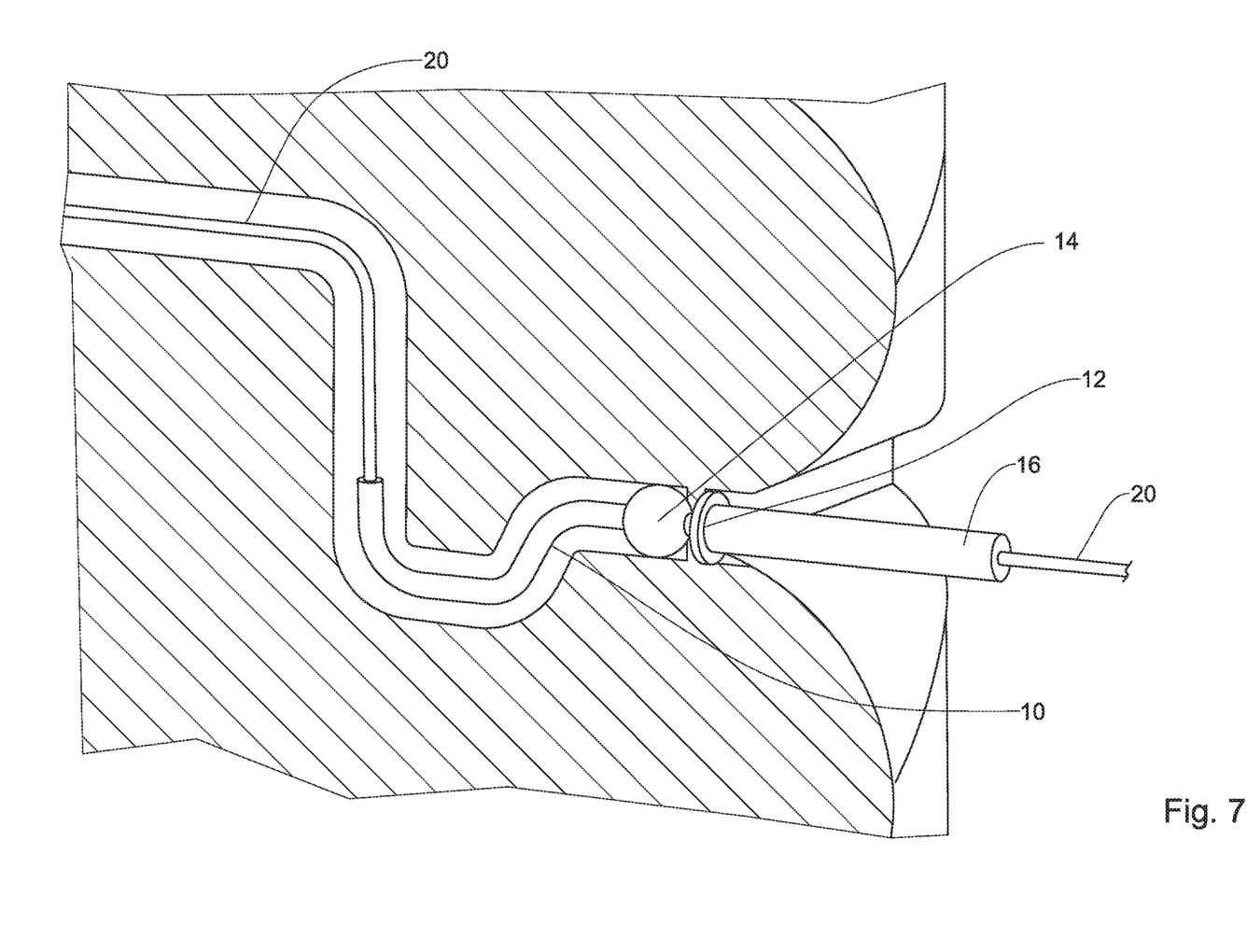
FIG. 7 shows the configuration of the sealing device according to a specific example of the invention.

Reference is made to FIG. 7, illustrating the insertion of the sealing device inside the colon. In this non-limiting example, the tip of the flexible sealing tube forms a shaped curve in the colon to keep a certain level of lubricating water as shown in the figure. The configuration enables an appropriate insertion of the sealing device of the present invention in the colon and a better sealing. This configuration also enables confining a water-based solution for the elongated carrier humidification.

In this specific example, the insertion procedure includes:

i) Insertion of a flexible sealing tube 10 into the colon until the rectal surface 12 contacts the anus. In the process of insertion, the sealing tube 10 achieves a curved shape originating from the natural shape of the colon. Rectal balloon 14 is inflated and locks the sealing device in place.

ii) An elongated carrier 20 or a tool is inserted into the sealing tube 10, and is configured to slide though the sealing tube 10 to reach the traverse colon. In some embodiments, the elongated carrier 20 or the tool advances along the colon based on the piston head propagation technique described in previous GI view applications.

The invention claimed is:

1. A sealing device, comprising:
   a sealing tube having proximal and distal terminal ends, said proximal terminal end being adapted to be inserted through an anus of a patient;
   a tightening mechanism, wherein the tightening mechanism comprises:
      a rectal balloon mounted on and in fluid communication with said sealing tube and inflatable to apply a force internally against the anus to generate a pressure seal; and
   a rectal sealer mounted to said sealing tube the rectal sealer including a handle configured for a user to handle the sealing device, the handle extending proximally from adjacent to the distal terminal end, the handle having a flat surface attached thereto and being substantially normal to an axis of the sealing tube and positioned at a distance from the rectal balloon that is variable during a procedure, wherein said flat surface is sized for contacting the anus to apply pressure to the anus externally effective to stimulate contraction of anal muscles while said rectal balloon is configured to concurrently apply said internal force, wherein said variable distance allows adjustment of the pressure applied externally to the anus.

2. The sealing device according to claim 1, wherein said sealing tube includes:
   a passageway connectable to a source of fluid pressure and being operable to convey fluid pressure into a colon when the sealing tube is inserted into the colon, said sealing tube thereby allowing application of said fluid pressure upon inner walls of the colon.

3. The sealing device according to claim 1, wherein said distance is selected to prevent escape of fluid pressure out of the colon.

4. The sealing device according to claim 1, wherein the sealing device is an integral part of an endoscopic system.

5. The sealing device according to claim 1, further comprising an elongated carrier arranged for sliding movement through the sealing tube.

6. The sealing device according to claim 5, wherein said elongated carrier includes at least one of the following configurations:

the elongated carrier includes a plurality of auxiliary tubes including at least one of an electrical cable, a hollow tube shaped to define a lumen for passage therethrough of a tool; or a hollow tube shaped to define a lumen for passage therethrough of a fluid; or the elongated carrier includes a passageway for passing therethrough of a tool selected from at least one of an endoscopic tool, an imaging device, an illumination device, a biopsy collecting tool, an optical device, a fluid device, or a treatment tool.

7. The sealing device according to claim 5, further comprising:

wherein the elongated carrier includes a passageway for passing therethrough a tool selected from at least one of an endoscopic tool, an imaging device, an illumination device, a biopsy collecting tool, an optical device, a fluid device, or a treatment tool; and at least one mechanical seal through which at least one of the elongated carrier or the tool passes, wherein said mechanical seal is accommodated within said sealing tube and is configured for preventing gas leakage.

8. The sealing device according to claim 5, further comprising:

wherein the elongated carrier includes a passageway for passing therethrough a tool selected from at least one of an endoscopic tool, an imaging device, an illumination device, a biopsy collecting tool, an optical device, a fluid device, or a treatment tool; at least one of said tool or said elongated carrier being humidified when in use by applying at least one of the following: at least one of said tool or said elongated carrier is coated with a hydrophilic coating; and a cavity containing water-based solution through which at least one of said tool or said elongated carrier passes; said sealing tube has a curved shape to thereby enable confining of the water-based solution in the sealing tube.

9. The sealing device according to claim 8, having at least one of the following configurations: said cavity is located within the handle having a handle axis, said rectal sealer and said sealing tube being mounted on the handle; said cavity includes a porous material for controlled humidification; or said cavity passes through a passageway conveying gas into a colon such that said gas contains water particles to thereby enable humidification of at least one of said tool and said elongated carrier.

10. The sealing device according to claim 1, wherein the sealing tube has at least one of the following configurations:

the sealing tube has a diameter selected to enable the passage of at least one of a tool or an elongated carrier therethrough;

the sealing tube has a length selected to enable insertion thereof such until reaching an end of a sigmoid colon curvature of the patient; or the sealing tube includes a sleeve reinforced by a spring element placed along a length thereof to provide a predetermined stiffness selected to enable insertion of the sealing tube through the anus and navigation of at least one of a tool or an elongated carrier within the colon; said tool having a certain stiffness such that the stiffness of said sealing tube being higher than the stiffness of at least one of said tool or said elongated carrier.

11. The sealing device according to claim 1, further comprising a stand configured to support the handle.

12. The sealing device according to claim 1, wherein the handle and the flat surface are integral with each other.

* * * * *